(12) United States Patent
Broers et al.

(10) Patent No.: US 6,928,742 B2
(45) Date of Patent: Aug. 16, 2005

(54) METHOD AND APPARATUS FOR FINDING THE POSITION OF A MECHANICAL AXIS OF A LIMB

(75) Inventors: Holger Broers, Bundesrepublik (DE); Werner Berner, Schweiz (DE); Bernhard Hauri, Schweiz (DE); Thomas Hauri, Schweiz (DE)

(73) Assignee: Plus Orthopedics AG (CH)

( * ) Notice: Subject to any disclaimer, the term of this patent is extended or adjusted under 35 U.S.C. 154(b) by 0 days.

(21) Appl. No.: 10/363,488
(22) PCT Filed: May 17, 2001
(86) PCT No.: PCT/EP01/05663
§ 371 (c)(1), (2), (4) Date: Aug. 11, 2003
(87) PCT Pub. No.: WO02/17798
PCT Pub. Date: Mar. 7, 2002

(65) Prior Publication Data
US 2004/0054442 A1 Mar. 18, 2004

(30) Foreign Application Priority Data
Aug. 31, 2000 (DE) .......................................... 100 42 965

(51) Int. Cl.$^7$ ............................................. A61B 5/103
(52) U.S. Cl. .......................... 33/512; 33/227; 600/587; 606/87; 606/89; 382/128
(58) Field of Search .......................... 33/512, 515, 227, 33/228, 203.18, DIG. 21; 600/587, 476; 382/128, 131; 606/87, 88, 89, 82

(56) References Cited
U.S. PATENT DOCUMENTS

| | | | |
|---|---|---|---|
| 5,007,912 A | * | 4/1991 | Albrektsson et al. .......... 606/87 |
| 5,265,034 A | * | 11/1993 | Breckenridge et al. .. 250/201.1 |
| 5,514,143 A | * | 5/1996 | Bonutti et al. ................ 606/86 |
| 5,682,886 A | | 11/1997 | Delp et al. |
| 5,847,976 A | * | 12/1998 | Lescourret ..................... 703/8 |
| 5,871,018 A | | 2/1999 | Delp et al. |
| 6,013,081 A | * | 1/2000 | Burkinshaw et al. ......... 606/88 |
| 6,385,475 B1 | | 5/2002 | Cinquin et al. |
| 6,554,837 B1 | * | 4/2003 | Hauri et al. ................... 606/87 |

FOREIGN PATENT DOCUMENTS

| | | |
|---|---|---|
| WO | WO 95/00075 | 1/1995 |
| WO | WO 99/23956 | 5/1999 |
| WO | WO 00/00093 | 1/2000 |
| WO | WO 00/27283 | 5/2000 |

* cited by examiner

Primary Examiner—G. Bradley Bennett
Assistant Examiner—Amy R. Cohen
(74) Attorney, Agent, or Firm—Knobbe, Martens, Olson & Bear LLP

(57) ABSTRACT

A method of finding the position of a mechanical axis running in the longitudinal direction through a limb that is rotatably supported by its first end in a center of rotation that is not fixed and is not accessible for the mechanical determination of coordinates, by means of an optical coordinate-measurement device with an indicator to detect measurement-point coordinates in one rotational position of the limb, such that, for each rotational position, a multi-point indicator rigidly attached near the second end of the limb signals several measurement-point coordinates, and, from the sets of measurement-point coordinates detected in a plurality of rotational positions, at least one group is selected that can be assigned to the same site of the center of rotation, and the measurement-point-coordinate sets assigned to this site of the center of rotation are used to calculate the mechanical axis.

20 Claims, 8 Drawing Sheets

Femur:

Frontal plane medial/lateral = $\alpha_F$ a)

Transverse plane transverse = $\beta_F$ b)

Sagittal plane ventral/dorsal = $\chi_F$ c)

Tibia:

| Frontal plane | Transverse plane | Sagittal plane |
|---|---|---|
|  |  |  |
| medial/lateral $= \alpha_T$ | transverse $= \beta_T$ | ventral/dorsal $= \chi_T$ |
| a) | b) | c) |

- Laptop for data collection and evaluation

- Optical detection system POLARIS with control unit

- Active sampler (transmitter) (adapter device)   • Passive sampler (transmitter)

METHOD AND APPARATUS FOR FINDING THE POSITION OF A MECHANICAL AXIS OF A LIMB

RELATED APPLICATIONS

This application is a national phase entry in the United States of the International Application PCT/EP01/05663 filed May 17, 2001 and claims the benefit of the German Patent Application No. DE100 42 975.3 filed Aug. 31, 2000.

BACKGROUND OF THE INVENTION

1. Field of the Invention

The invention relates to a method and an apparatus for finding the position of the mechanical axis of a vertebrate limb running in a longitudinal direction through a limb that is rotatably supported by its first end in a center of rotation that is not fixed and is not accessible for the mechanical determination of coordinates by means of a optical coordinate measurement device with an indicator to signal measurement point coordinates in one rotational position of the limb.

2. Description of the Related Art

The mechanical axes of limbs, such as a human femur, must be known in order to insert prostheses/implants, such as a knee prosthesis, correctly. The resection that prepares the way for installation of the knee prosthesis on the femur must be oriented in accordance with the orientation of the femur's mechanical axis. Ordinarily the frontal regions of the femur are resected. However, at least one so-called dorsal and one ventral cut are also made at the femur, because the femoral component of knee prostheses is customarily U-shaped.

The exact position of the resection surfaces at the femur is of crucial significance for a long working life of the knee prosthesis. So far even an experienced surgeon finds the performance of this resection extremely demanding, because during the operation the standard bearing surfaces must be established according to the geometrical specifications of the knee prosthesis while taking into account the mechanical axis, and in some cases pathological displacements must also be corrected and allowances must be made for the position and action of the ligaments and muscles that are present.

Known sets of instruments for the implantation of knee prostheses comprise resection accessories in the form of cutting jigs that help the surgeon to guide a saw blade. For this purpose the cutting jigs are aligned as accurately as possible according to the mechanical axis of the femur, with the aid of various devices.

An apparatus of this kind to assist alignment of the cutting jig is disclosed in the document WO 00/00093. This apparatus consists substantially of a base part that can be releasably fixed in the distal region of the femur and a reference element that is connected to the base part so as to be pivotable and/or longitudinally displaceable, and that comprises a means of specifying a coordinate system. The reference element can be oriented so that its position is fixed precisely with respect to the femur, and the means for specifying the coordinate system are so configured that they can be used determine the orientation in which tools such as a cutting jig are attached.

A reference element of this kind is firmly connected to the femur and is aligned with the femur's mechanical axis. A locating rod is used to measure the mechanical axis. This locating rod is connected at its first end to the reference element, and its second end is directed toward the head of the femur, which is seated in the hip and through which the mechanical axis of the femur runs. In order to point the locating rod toward the head of the femur, the pelvic ridge is first palpated by the "two-finger" method. The disadvantage of "two-finger" palpation is that it is relatively inexact.

The patents U.S. Pat. Nos. 5,871,018 and 5,682,886 disclose methods for finding the position of the femoral mechanical axis. According to these procedures, in a first step the coordinates of the femur are measured, for example from an image obtained by computer-assisted tomography, and are stored in a computer. The stored data are then used to generate a three-dimensional computer model of the femur, and on the basis of this model the optimal coordinates are found for attaching to the bone a jig as well as the knee prosthesis that will eventually be installed. The basis for this operation is specification of the mechanical axis of the femur.

After such a simulation the patient's femur is fixed in position, and a recording device is used for the tactile sampling of individual points on the femoral surface in order to establish the orientation of the femur for the operation that is to be performed. This scanning of the bone requires either that the femur be exposed for much of its length, if possible as far as the hip joint, so that its surface is accessible to the recording device, or else that a kind of needle be used to pierce the skin and contact the bone as a sampling instrument. However, because any surgical intervention presents a risk to the patient, and insertions of a needle cause bleeding and hence an increased danger of infection of the associated bones, it is undesirable to carry out an additional surgical intervention in the hip region or to insert needles along the femur in order to find the position of the center of rotation. Furthermore, in this process the femur must be firmly fixed to the platform of the recording device, because otherwise the hip socket can be displaced during the fixation of the various instruments, so that after the femoral coordinates have been recorded, the cutting jig would be wrongly positioned.

The document FR 2 785 517 describes a method and an apparatus for detecting the center of rotation of the femoral head in the hip socket. For this purpose the femur is moved so that its head shifts within the socket, and the coordinates measured for various positions of the femur are recorded. As soon as shifting of the center of rotation of the femur occurs, a corresponding counterpressure is applied to the head of the femur, and this is taken into account for the specification of a point that is related to the position of the femur.

The objective of the present invention is to develop a method of this generic kind further, in such a way that it permits a rapid and simple acquisition of the information needed for the anatomically correct installation of an implant in dependence on the orientation of the mechanical axis of the limb, and also to disclose an arrangement for implementation of this method.

SUMMARY OF THE INVENTION

This objective is achieved by a method according to claim 1 and by an apparatus according to claim 11.

An point of the invention lies in the fact that from the various sets of measurement-point coordinates recorded by means of the multiple-point indicator attached to the limb in several rotational positions of the limb, at least one group is selected that can be assigned to a fixed center of rotation. The sets of coordinates assigned to a fixed center of rotation are used to calculate the mechanical axis of the limb.

Because at least one group has been selected from the sets of measurement-point coordinates, it is possible to reject erroneous measurements, or measurements showing major deviation, by means of an iterative error-minimizing calculation, for the fixed center of rotation to be established. Hence, for example even though the patient's pelvic area, within which the center of rotation is situated, might be displaced during the rotation of the leg, a fixed center of rotation can be identified from the measure-point coordinates.

In order to find the position of the mechanical axis two points are established through which the mechanical axis passes. The first point is a reference point at the distal end of the femur, the location of which is found by tactile scanning of the femoral surface; that is, its position is determined from those of the epicondyle and Whiteside line near the knee joint. This reference point is easily found, because the distal end of the femur is exposed in any case in order to install the knee prosthesis. The second point is represented by the center of rotation established with reference to the groups of measurement-point-coordinate sets.

In order to find this point, for each rotational position of the femur the measurement device is used to detect the measurement-point coordinates by means of the multiple-point indicator (active or passive transmitter) attached to the distal end of the femur. For this purpose, for example, an active transmitter emits radiation from several radiation sources for each rotational position. The radiation sources, for instance IR-LEDs, are disposed on the base body at fixed distances and angles with respect to one another. In another application the active transmitters can also be replaced by one or more passive transmitters.

A calibration of the measurement-point indicator, carried out before the actual measurement has begun, provides measurement-point coordinates that reproduce the distance and the angular positions of the above-mentioned radiation sources with respect to one another on the multiple-point indicator. The measurement-point coordinates obtained from this calibration are compared, within a single coordinate system, with the measurement-point coordinates detected in each rotational position. Subsequently those of the detected measurement-point coordinates that lie outside a prespecified tolerance range of the calibration measurement-point coordinates are eliminated; this measure is intended to exclude major errors in measurement that could be introduced, for example, by extraneous reflexes.

The multiple-point indicators employed in the proposed method and the proposed apparatus have at least three, preferably four active or passive radiators (emitters or reflector elements), the output of which is recorded by the associated measurement device—specifically, two cameras fixedly spaced apart from one another on a camera beam. Each of the emitters or reflectors is mounted on a base structure in a fixed spatial relation to the others. Because the base structure itself is in turn fixedly attached to the end of the limb for which the center of rotation and mechanical axis are to be determined, the spatial distribution of the "measurement points" amounts to a representation of movement paths with a fixed relation to one another, when the limb to be investigated is pivoted about its center of rotation. The operator arrests the movement of the limb (i.e., for example, the leg of the patient with multi-point indicator attached to the distal end of the femur) briefly when each of several rotational positions has been reached, and the measurement device then delivers an image showing the associated position of each individual measurement point.

If the center of rotation had been precisely fixed during this procedure, all the measured points would lie on spherical surfaces around the center of rotation, and determination of its position would be fairly trivial. In practice, however, such fixation is not or at least not strictly achievable; instead, during the stepwise pivoting movement the center of rotation is repeatedly displaced. An element of the invention is to extract groups of measurement-point coordinate sets, each of which can be ascribed to a common center of rotation. Whereas for a fixed center of rotation it would not be strictly necessary to use multi-point indicators, the method in accordance with the invention does prefer such indicators to be employed. The sets of coordinates that they provide enable the evaluation involving averages in the error-minimizing calculation to be performed with a high degree of robustness and precision. From those sets of measurement-point coordinates that can be assigned to a group, in a calculator device that forms part of the measurement apparatus several spherical surfaces are calculated, which represent the movement paths of the second end of the limb to which the indicator is attached. With the aid of these spherical surfaces the associated center points can be calculated simply and rapidly. The calculated center points correspond to the centers of rotation of the femur, or those relative to the active and/or passive transmitter. This procedure makes it possible rapidly and easily to locate the center of femoral rotation in the pelvic acetabulum, which is needed to specify the orientation of the mechanical axis, with no need for extra surgery in the patient's hip region.

Once the mechanical axis of the femur has been calculated with high precision as described above, a cutting jig to be attached to the distal end of the femur is aligned with respect to that axis so that it can subsequently guide a cutting device (saw) in directions as precise and anatomically correct as possible, relative to the mechanical axis. For this purpose the cutting jig can be connected by way of a connecting piece to the holder for the fixed multi-point indicator, which has already been attached to the distal end of the femur, and/or can be aligned by means of a supplementary caliper device.

In both cases the result is an alignment of the multi-point indicator and/or the cutting jig within a global coordinate system, i.e. one with its origin outside the patient. This determines, among other things, the way that a local coordinate system with its origin in the multi-point indicator is disposed relative to the center of rotation corresponding to the midpoint. Because the jig and the cutting device guided therein can be aligned precisely with respect to the previously calculated mechanical axis, the knee prosthesis can be inserted and positioned against the cut surfaces of the femur with high precision in accordance with the mechanical axis.

As a result of such a geometrically correct and precise installation of the knee prosthesis, the patient will experience improved mobility after the operation as well.

Because of the selection of a group of measurement-point-coordinate sets such that as many as possible of these sets, each of which represents one rotational position of the femur, are combined with one another and each such group of measurement-point-coordinate sets is related to a center of rotation that has not been displaced, if the center of rotation is displaced during the measurement and/or between the measurement and the positioning of the cutting jig, owing to a change in the patient's position while the center of rotation is being measured, this fact can be recognized and the possibility that it will introduce error into the specification of the mechanical axis can be excluded.

In a preferred embodiment of the invention there are several repetitions of the step of selecting one group from the set of measurement-point coordinate quantities recorded in a plurality of rotational positions. After each selection step the particular set of measurement-point coordinates that shows the greatest deviation from the coordinates of calculated measurement points is rejected. The deviation to be calculated for this purpose, as well as various vector parameters for calculation of the coordinates of the center of rotation, which is assumed to be fixed, in the local and the global coordinate system are determined by means of iterative calculation according to the least-squares method. This procedure makes use of the basic idea underlying the error-minimizing calculation, namely that approximate values for the quantities to be measured are determined from erroneous measured values in order to specify an improvement of the quantities to be measured (measurement-point coordinates) relevant to the deviation.

Important unknowns are a local translation vector, associated with translation of a measurement point situated in the local coordinate system (the origin of which is situated in the active or passive transmitter), into the global system, as well as a global translation vector and a rotation matrix. The last two quantities serve to describe the translation of a measurement point to the rotation point in the global system, and the rotations of the local system within the global system. The application of an iterative calculation in determining the center of rotation makes possible a largely error-free determination of the center of rotation, even if the patient moves during the measurement.

An important boundary condition is the use of sterile measurement tools as well as an electronic/optical measurement device in combination with the calculation device, which enables a more rapid completion of the measurement on the basis of optical data-transmission routes and electronic data processing, which in turn reduces the time required for the operation.

The mechanical axis is determined with the computer-assisted optical measurement device. It is defined by the center of rotation and the additional reference point at the distal end of the femur. Susequently, during the surgical procedure, the cutting jig is positioned by means of the measurement device in such a way that the structures for mechanical guidance of the cut are in the correct spatial orientation with respect to the patient's mechanical axis. This makes it possible for the cut to be made so precisely that the deviation with respect to the mechanical axis is less than 1°.

BRIEF DESCRIPTION OF THE DRAWINGS

In the following some exemplary embodiments of the invention are described with reference to the attached drawings, wherein.

DETAILED DESCRIPTION OF THE PREFERRED EMBODIMENTS

Figure 1:
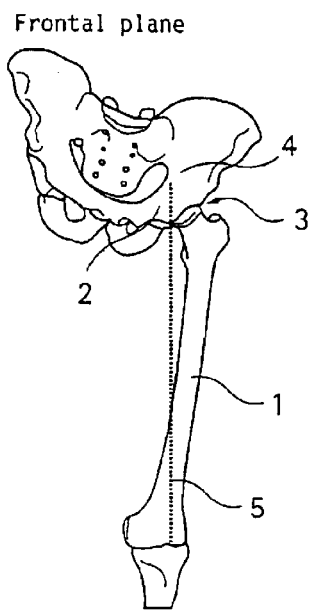
FIG. 1 shows the mechanical axis of the femur.
Figure 1:
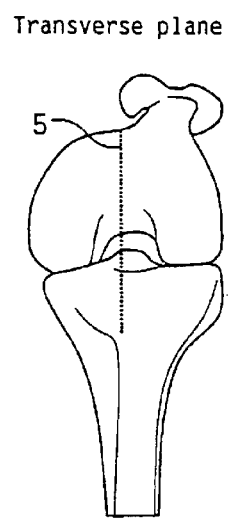
Figure 1:
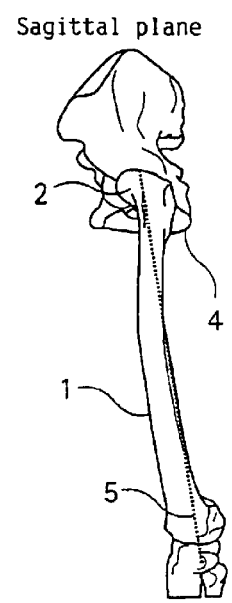

FIG. 1 shows how a mechanical axis of the leg of a healthy person is disposed with respect to the femur 1. The mechanical axis 5, drawn with a dashed line, in part (a) is seen from the front, so that its orientation in the medial/lateral direction $\alpha_F$ is evident. The mechanical axis 5 is specified by a center of rotation 3 of a femoral head 2 in the socket of a hip joint 4, and by bony reference points in the region of the knee (distal end of the femur).

In the transverse plane, shown in part (b), the direction $\beta_F$ of the mechanical axis is defined by the piercing point or by the Whiteside line and the direction of the epicondylar axis or dorsal condylar axis.

In the sagittal plane, shown in part (c), the ventral/dorsal direction $\chi_F$ of the mechanical axis is fixed by the center of rotation 3 of the femoral head 2 and by bony reference points on the femur in the knee region, as in the frontal plane.

Figure 2:
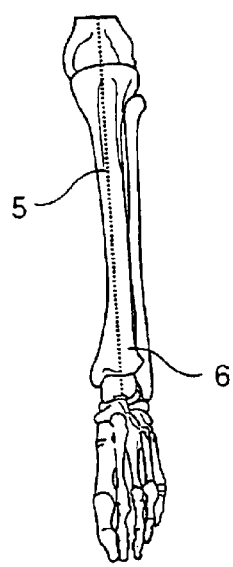
FIG. 2 shows the mechanical axis of the tibia.
Figure 2:
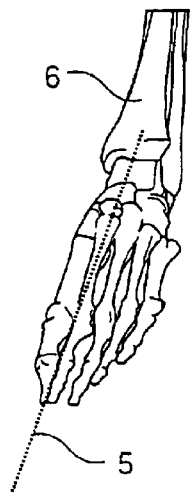
Figure 2:
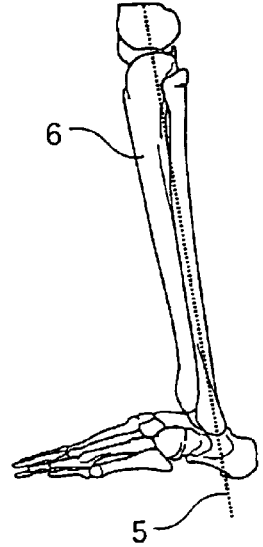

FIG. 2 shows, as another example of a mechanical axis of a limb in the human body, that of a tibia 6. In the frontal plane shown in part (a) the medial-lateral direction $\alpha_T$ of the mechanical axis 5 is defined by the center of gravity of the malleolar axis and the piercing point of the mechanical axis 5 and corresponding bony reference points on the tibial side of the knee joint. In the transverse plane, shown in (b), the direction $\beta_T$ of the mechanical axis is established by the following alternatives:
1. metatarsal ray,
2. malleolar axis, tilted by 23°,
3. line perpendicular to the axis of rotation of the ankle joint, or
4. on the basis of the tuberosity.

In the sagittal plane, shown in (c), the ventral/dorsal direction $\chi_T$ of the mechanical axis 5 is defined by the axis of the upper ankle joint and the point at which the axis 5 intersects the tibial plateau, as well as the front edge 6 of the tibia.

From the two examples of a specified mechanical axis presented above it will be evident that it is relatively simple to identify the points that determine its orientation when the bones and joints are exposed. However, in order to avoid a supplementary surgical invention, such as would otherwise be necessary to determine the center of rotation 3 in the region of the hip joint, it is a substantially more complex matter to identify the rotation-center coordinates in each of the planes presented above exclusively by observing the movements of the limb.

An additional consideration is that according to the state of the art, for reliable specification of the mechanical axis the center of rotation should not change its position during the movements of the femur that are needed to carry out the mechanical-axis specification; otherwise the measurement procedure would have to be repeated from the start. This applies likewise to the time between completion of the measurement and the positioning of the cutting jig on the femur according to the mechanical axis thereby specified.

As mentioned above, for the femur the orientation of the axis 5 is defined by the center of rotation of the femoral head 2 in the hip socket and an axis point situated at the distal end of the femur, in the region of the knee. Because the distal end of the femur has been exposed in any case, in order to insert the knee prosthesis, the axis point situated here is defined by bony references. Here the term "bony references" denotes special points at the distal end of the femur, which are situated in a known relation to the femoral mechanical axis and can be selected and localized by the operator on the basis of previous experience. Such a reference point is signalled by touching the multi-point indicator to the distal end of the femur. This multi-point indicator serves to find the measurement-point coordinates associated with a bony reference when the femur is in a particular rotational position. This movable multi-point indicator (feeler) bears LEDs or punctate reflectors at several points, the light from which is detected by a remote optical receiving system; the points thus detected are assigned coordinates in a coordinate system.

Because the head of the femur is not accessible during the knee operation, the center of rotation 3 of the femur must be identified by indirect kinematic means. For this purpose the position of the femur when rotated by various amounts is measured by the measurement device that defines the origin of a global coordinate system.

Figure 3:
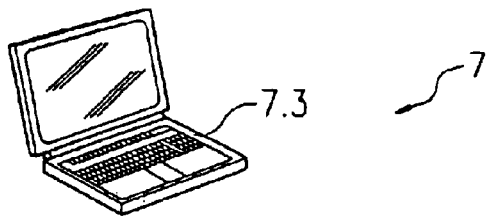
FIG. 3 is an illustration of a measurement arrangement according to one embodiment of the invention.
Figure 3:
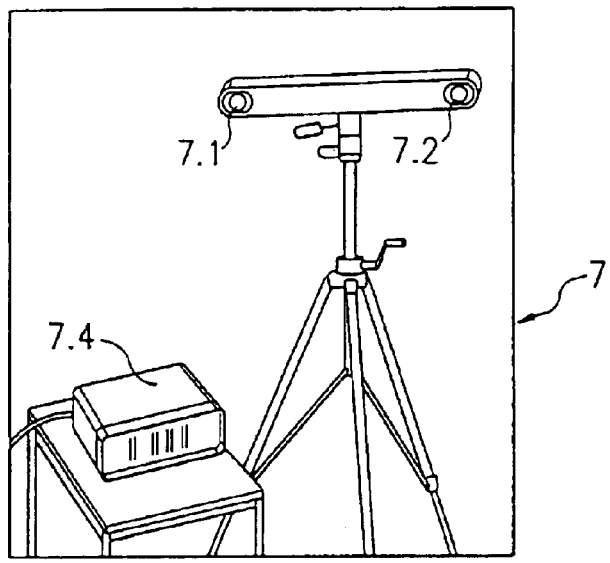
Figure 3:
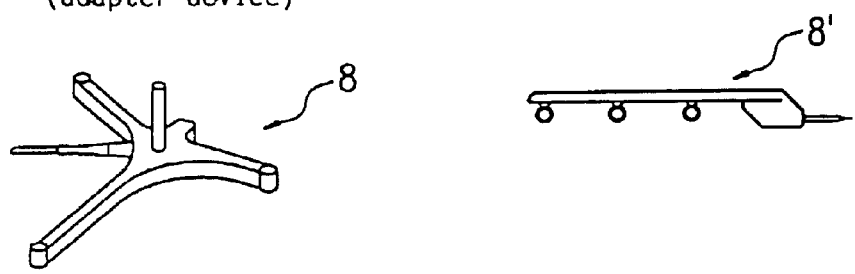

Elements of such a measurement device are shown in FIG. 3. It comprises the multi-point indicators 8 and 8' mentioned above, with several light-emitting diodes or small reflector elements as coordinate-signaling units, an optical reception system 7 with two cameras 7.1, 7.2 on a camera beam as well as a control unit 7.4 that serves to receive the radiation emitted by the LEDs, and a data collection and evaluation unit 7.3, for instance in the form of a laptop computer. It is necessary for the measurement device to have a working range of ca. 0.5 m×0.5 m×0.3 m and a point measurement accuracy of ca. 0.5 mm. Such a device is known per se and is marketed, for example, by Northern Digital Inc. under the name "Hybrid POLARIS". Experiments have shown that its measurement accuracy is ca. 0.25 mm, so that this device meets the requirements for use in the positioning of a knee prosthesis.

Figure 4:
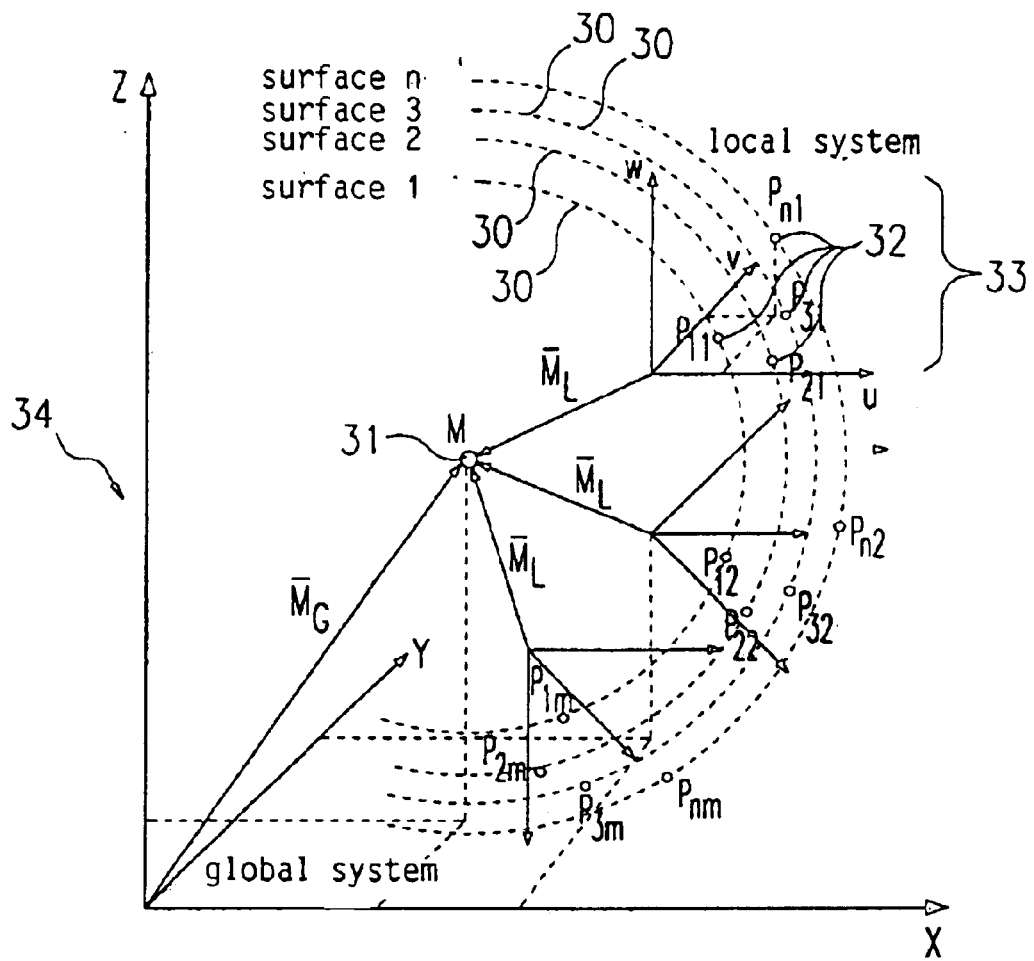
FIG. 4 is a diagram of the coordinate systems that serve as a basis for calculation of the center of rotation in accordance with the invention.

FIG. 4 shows a global and a local coordinate system, which serve as a basis for calculating the coordinates of the center of rotation in accordance with the invention. The multi-point indicator rigidly connected to the femur, together with the measurement-point field $P_{nm}$ comprising the fixedly spaced-apart points $P_{11}$–$P_{n1}$, $P_{12}$–$P_{n2}$, $P_{1m}$–$P_{nm}$ (where n=number of measurement points on the multi-point indicator, m=number of femoral positions), comprises a local coordinate system 33. During the rotational movements of the femur the multi-point indicator moves over the spherical surfaces 1, 2, . . . n about the point to be specified, namely the central point 31 or rotation point M, which corresponds to the center of rotation 3 in the vicinity of the hip joint. The rotation point M can be described by the global translation vector in the global coordinate system 34

$$\vec{G} = (X, Y, Z),$$

and by the local translation vector $$\vec{L} = (u, v, w).$$

Figure 5:
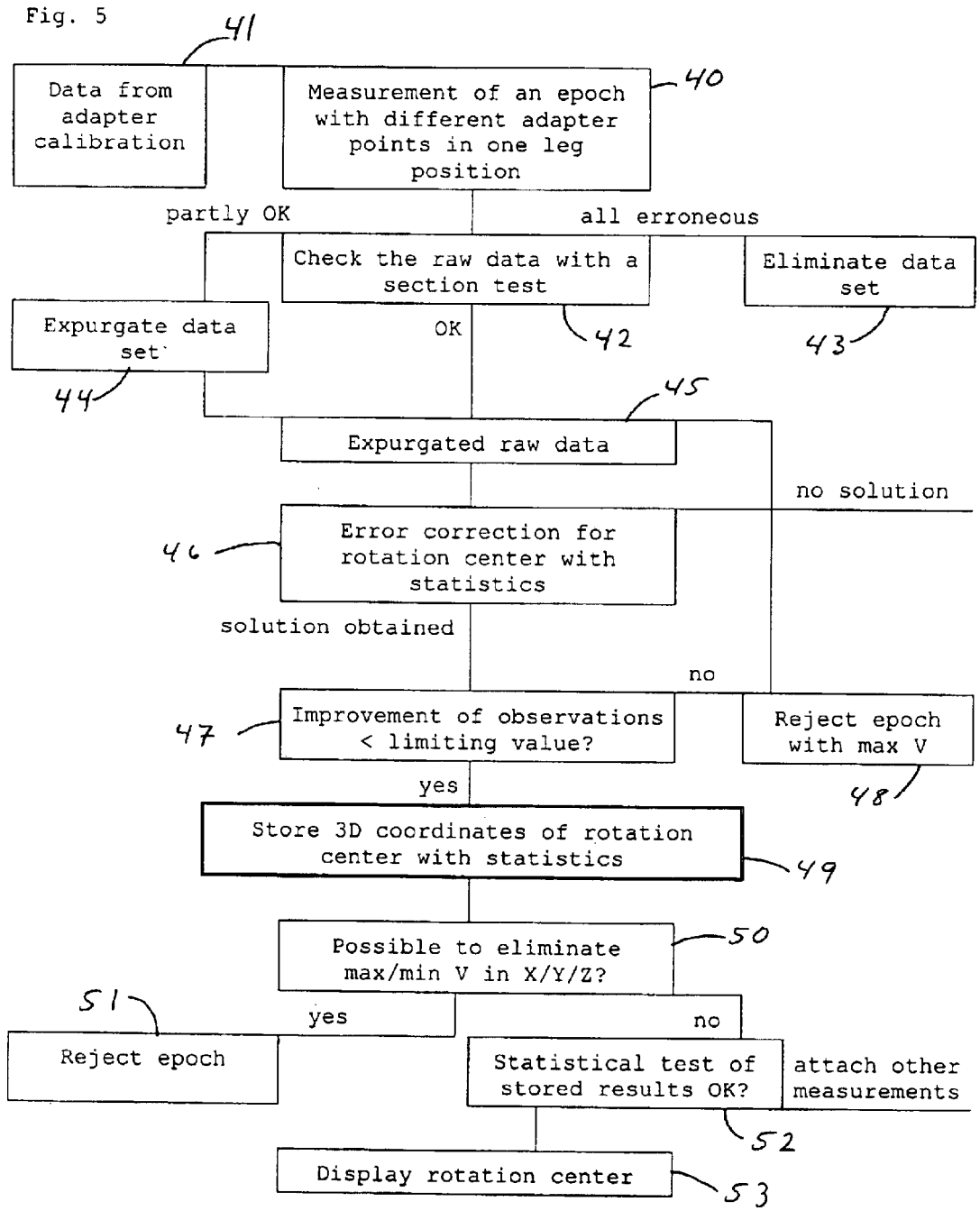
FIG. 5 is a flow chart to show the sequence of events involved in specifying a mechanical axis in accordance with the invention.

FIG. 5 is a flow chart to show the sequence of steps in specifying the center of rotation. In one step 40 the coordinates of the measured points indicated by the measurement device for a particular rotational position of the femur are input by means of the transmitter (p/a) and the optical receiver/transmitter system, so that they can be processed further there by means of a data collection and evaluation device.

First, in a step 41, the transmitter is calibrated by entering the distances and angles of the individual points with respect to one another on the multi-point transmitter (p/a) in the local coordinate system. This is done by system output. The measurement-point coordinates resulting from this calibration are then, in a step 42, compared by a so-called section test with those found for a particular rotational position. Subsequently those measurement-point coordinates lying outside a tolerance limit, which has been specified in advance as a result of the calibration, are extracted or corrected; the data set can thus be expurgated. Alternatively, the whole data set comprising measurement-point coordinates that refer to a given rotational position of the femur (measurement-point-coordinate set) can be discarded in a step 43, and new measurement of the point coordinates in a particular femoral rotation position can be carried out. Hence the step 42 serves to eliminate those measurement-point coordinates that contain severe measurement errors.

The raw measurement-point-coordinate data available in step 45, whether obtained directly from step 42 or after expurgation in step 44, are now subjected to an iterative error-minimizing calculation in order to find the center of rotation and thus to specify the mechanical axis (step 46).

The error-minimizing calculation is employed to check the preliminary results for errors in the coordinate measurements and to determine their accuracy. The measured coordinates are regarded as potentially erroneous because the patient should be allowed to move during the measurement process, but any such movement might involve displacement of the center of rotation.

The iterative calculation is performed by the least-squares method. The procedure is as follows:

A measurement point, or a set of measurement-point coordinates P, is measured by the optical receiving apparatus and is described in the global coordinate system with the following position vector:

$$\vec{P_G} = \begin{pmatrix} x_P \\ y_P \\ z_P \end{pmatrix} \quad (1)$$

The 3D measurement-point coordinate, as mentioned above, has been specified in advance with reference to the local coordinate system, as the position vector $\vec{P_L}$:

$$\vec{P_L} = \begin{pmatrix} u_P \\ v_P \\ w_P \end{pmatrix} \quad (2)$$

The three unknown parameters that also enter into the calculation are as follows:

the rotation of the local coordinate system within the global coordinate system, described in three-dimensional space by a rotation matrix R:

$$R = \begin{pmatrix} a_{11} & a_{12} & a_{13} \\ a_{21} & a_{22} & a_{23} \\ a_{31} & a_{32} & a_{33} \end{pmatrix} \quad (3)$$

the translation of the rotation point M in the global system, on which are centered the spherical surfaces associated with the rotational movement paths of the femur:

$$\vec{M_G} = \begin{pmatrix} X_M \\ Y_M \\ Z_M \end{pmatrix} \quad (4)$$

the translation to the rotation point L in the local system:

$$\vec{M_L} = \begin{pmatrix} u_M \\ v_M \\ w_M \end{pmatrix} \quad (5)$$

In order to calculate the unknowns and the squares of the errors or improvement values v derived therefrom, a system of equations is set up on the basis of the following equation of condition:

$$\vec{P_G} = R*(\vec{P_L} - \vec{M_L}) + \vec{M_G} \quad (6)$$

When the coordinate parameters according to equations (1) to (5) are entered into the equation of condition, in vectorial representation, the following equation results:

$$\begin{pmatrix} X_P \\ Y_P \\ Z_P \end{pmatrix} = \begin{pmatrix} a_{11} & a_{12} & a_{13} \\ a_{21} & a_{22} & a_{23} \\ a_{31} & a_{32} & a_{33} \end{pmatrix} * \begin{pmatrix} u_P - u_M \\ v_P - v_M \\ w_P - w_M \end{pmatrix} + \begin{pmatrix} X_M \\ Y_M \\ Z_M \end{pmatrix}$$

By summation of the observed values $X_P$, $Y_P$ and $Z_P$ with the improvement values $v_x$, $v_y$ and $v_z$, the following corrective equations are obtained:

$$\vec{X_P} = X_P + v_x = a_{11}(u_P - u_M) + a_{12}(v_P - v_M) + a_{13}(w_P - w_M) + X_M + v_x$$

$$\vec{Y_P} = Y_P + v_y = a_{21}(u_P - u_M) + a_{22}(v_P - v_M) + a_{23}(w_P - w_M) + Y_M + v_y$$

$$\vec{Z_P} = Z_P + v_z = a_{31}(u_P - u_M) + a_{32}(v_P - v_M) + a_{33}(w_P - w_M) + Z_M + v_z$$

In the calculation according to the least-squares method, the sum of the squares of improvement values is now calculated, the improvement values having been derived from the standard deviation of the unknowns $$S_x = S_0 * \sqrt{Q_{ii}}$$

where $Q_{ii}$ represents the diagonal elements of a design matrix, and hence the standard deviation of a weighting unit is $$S_0 = \sqrt{\frac{v^T P v}{n - u}},$$

where P is the weighting of the observation, n is the number of observations and u is the number of unknowns.

The sum of the squares of the improvement values is then partially derived according to the above-mentioned unknowns, and to find the minimum of the sum these derivatives are set equal to zero. The result is a system of equations in the unknowns that are solved for the unknowns. With these solutions it is then possible to calculate estimated values for the measurement-point coordinates that are to be measured. The values of the unknowns thus obtained give the coordinates of the center of rotation, represented by the center point M of the global coordinate system shown in FIG. 4.

Each of the measurement-point-coordinate sets $P_{11}$–$P_{n1}$, $P_{12}$–$P_{n2}$, $P_{1m}$–$P_{nm}$ found for a particular rotational position of the femur is tested to see whether the improvement values associated with this measurement-point-coordinate set are below a limiting value that has been predetermined by the measurement accuracy of the measurement device 7 (step 47). If this is not the case, it follows that the center of rotation has shifted between the measurements in two rotational positions. The measurement-point-coordinate set that shows the maximal improvement values is rejected in a step 48; each of these considerations can be applied separately for a specific coordinate direction X or Y or Z.

Whenever it has been found in step 47 that the improvement values of a measurement-point-coordinate set are indeed within the acceptable limits, in a step 49 the 3D coordinates of the relevant center of rotation are stored in combination with a statistic.

When in the above-mentioned step 48 a measurement-point-coordinate set with maximal improvement values is rejected, a new calculation is carried out beginning at step 45, after several measurement-point-coordinate sets have been selected. This step of resuming the calculation is repeated until it is no longer possible to combine measurement-point-coordinate sets by collecting them into a group. This stage is identified in step 50. If the conclusion obtained in step 50 is that a further grouping of measurement-point-coordinate sets is possible, then in step 51 an arbitrary measurement-point-coordinate set is rejected and, beginning at step 45, a calculation is once again carried out. When step 50 finally indicates that all combinations of measurement-point-coordinate sets have been tested, in a step 52 the stored results are again examined to determine whether they are statistically within prespecified tolerance ranges. Then the procedure described above is repeated for all the other coordinate directions, so that ultimately in step 53 the calculated coordinates of a center of rotation are indicated.

An advantageous aspect of the method in accordance with the invention is the robust approach to error minimization, which results from the employment of a transmitter bearing multiple measurement points spaced apart from one another by a fixed distance, so that there is a fixed relationship between the observations in the system of equations involved in the error-minimizing calculation. As a result, it is possible to calculate the center of rotation and to find the orientation of the mechanical axis even if the hip moves.

As soon as the center of rotation has been established in this way, an imagined axis can be drawn through the point at the center of rotation and the previously determined reference point on the femur side, at the distal end of the femur.

Figure 6:
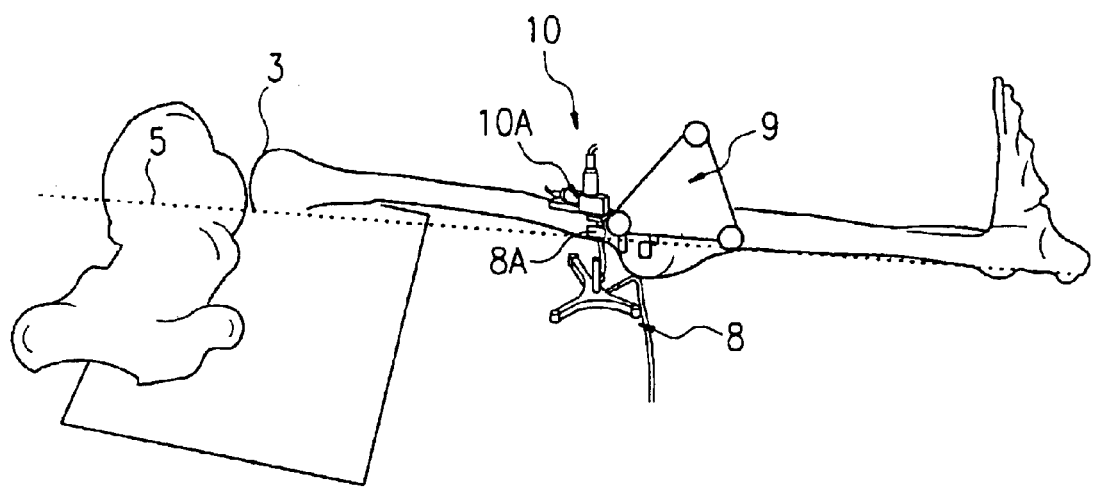
FIG. 6 shows a cutting jig with multiple indicators, attached to the femur.

FIG. 6 shows the cutting jig 10, which is kept in position with respect to the identified mechanical axis 5 of the femur 1' by means of a jig adapter 10A that is fixed to a holder 8A, which also supports the multi-point indicator 8.

The alignment of the cutting jig 10 with respect to the identified axis 5 of the femur is achieved by means of a second indicator 9. This allows the plane of the cutting jig to be adjusted so that it is perpendicular to the mechanical axis. In this process the orientation of the axis 5 in three dimensions is considered. With the second indicator 9 (jig-adapter device) the measurement-point coordinates found by tactile sampling with the measurement device 7 in the jig coordinate system are transmitted to the computer-assisted cutting jig 10. These results can then be processed further for reference in subsequent activities involving the cutting jig 10, such as aligning it with respect to the mechanical axis. Once the cutting jig has been correctly positioned, the goal of specifying well-defined cutting planes has been achieved.

Figure 7:
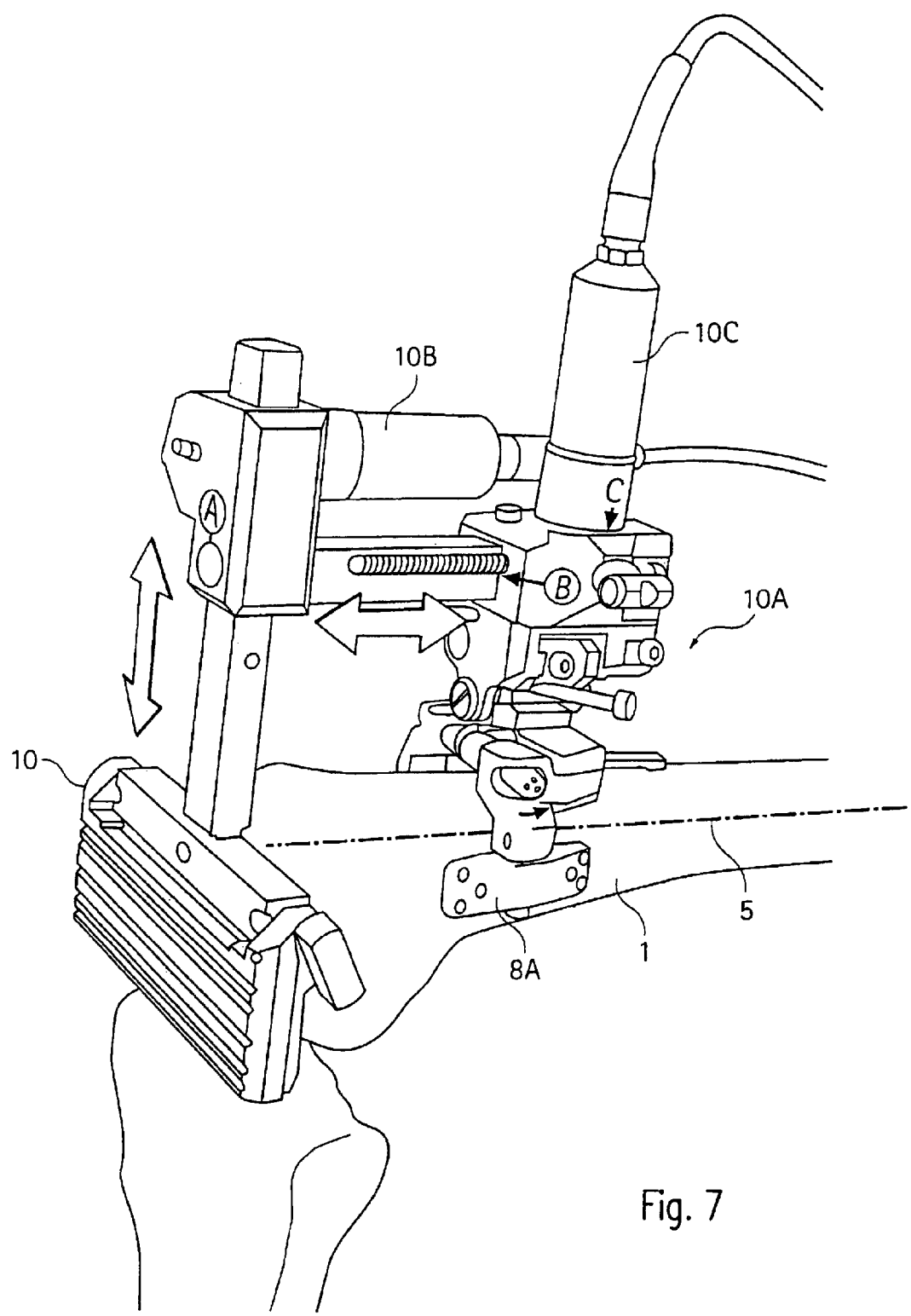
FIG. 7 shows a cutting jig including a device with which to position it at the distal end of the femur.

FIG. 7 shows in greater detail the structure of an arrangement for positioning the cutting jig 10 at the distal end of the femur 1, according to a preferred embodiment. The picture shows clearly the shape of the clamping device 8A that is fixedly attached near the distal end of the femur and that bears on one side (during the measurements to determine the mechanical axis) the multi-point indicator 8 shown in FIGS. 3 and 6, and on the other side (during the subsequent resection stages) the cutting jig 10.

On the clamping device 8A is mounted the calibratable jig adapter 10A, the angle-adjustment means (not identified individually) of which permit both an adjustment of the angle of inclination of the cutting-jig plane with respect to the axis 5 and a rotation of the cutting jig about that axis. After the cutting jig 10 has been successfully aligned in space, two electric motors 10B and 10C—in combination with linear drive means (not separately identified)—can be used to displace the cutting jig 10 longitudinally with respect to the latter's axis of orientation as well as perpendicular thereto. As a result, the cutting jig 10 is brought into the resection positions suitable for a prosthesis of the size that has been judged optimal for the particular patient. In these procedures, again, it is possible to determine precisely each position of the cutting jig, by tactile sampling with a movable multi-point indicator or feeler 8' (FIG. 3).

Figure 8:
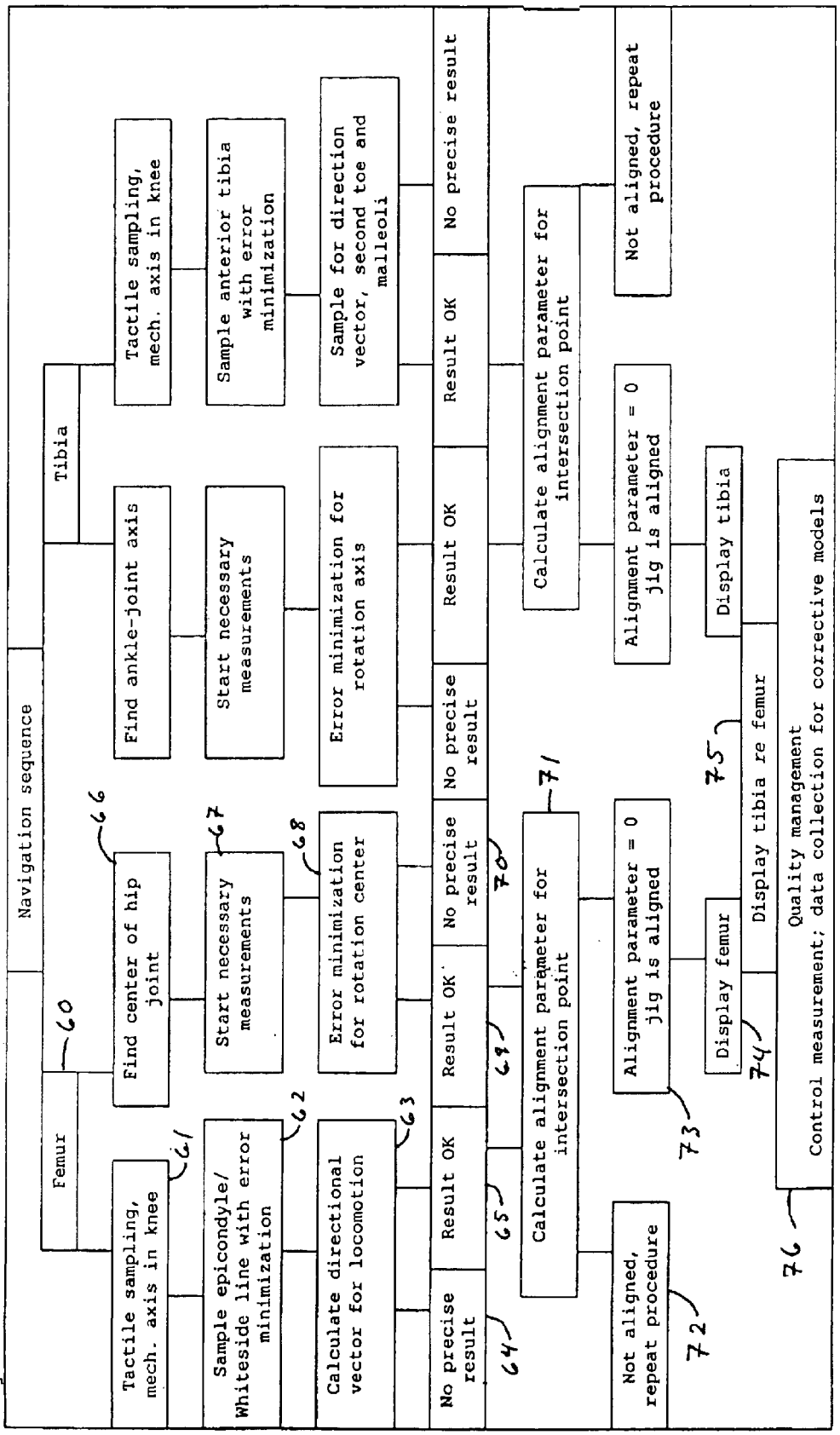
FIG. 8 is another flow chart to show the sequence of events involved in carrying out the method in accordance with the invention.

FIG. 8 shows another flow chart, which once again diagrams in rough strokes the individual steps in a preferred performance of the method in accordance with the invention. For more detailed explanation, the flow chart applies to an approach on the left side with respect to the femur.

First, in a step 61, the reference point at the exposed end of the femur in the region of the knee is touched. The subsequent step 62 involves tactile sampling of the epicondyle and Whiteside line, and in a step 63 the directional vector of locomotion is calculated.

In case no precise result is obtained from these steps 61 to 63, in a step 64 there is a loop back to step 62 for repetition of this step. If a precise result is obtained in step 65, then in step 71 this result is combined with that obtained from step 69 with respect to the calculation of the second point of the mechanical axis, namely the center of rotation, so that the mechanical axis can be calculated and hence the alignment of the cutting jig, which depends on that of the mechanical axis, can be determined.

So that the center of rotation can be determined in step 66, the necessary measurements are made in a step 67, with the femur in each of its various rotational positions, and the measurement-point coordinates thus obtained are processed in a subsequent error-minimizing calculation in step 68. Here, again, if no precise result is found in step 70, a loop leads back to step 67.

In step 73 the cutting jig is aligned about the axis of rotation, and then the anatomical configuration is displayed to the operator together with the data obtained, representing the femur alone in step 74 and the femur plus tibia in step 75.

The sequence of steps described above in the procedure to determine the mechanical axis of the femur and to position the cutting jig takes place, in a preferred embodiment of the method, in the context of interactive menu guidance, such that the individual steps to be carried out and the intermediate results of the steps are displayed to the operator, as well as certain elective options. The input from the operator's side is accomplished by way of a keyboard and/or foot-switch, or where appropriate by verbal instructions. The menu guidelines preferably combine clear color graphics, which can easily be viewed from the place occupied by the surgeon at the operation table, with acoustic signals (e.g. to confirm inputs or as a signal that usable measurement results have become available).

All the characteristics disclosed in the application documents are claimed as essential to the invention insofar as they are new to the state of the art individually or in combination.

List of Reference Numerals

1 Femur
2 Femoral head
3 Center of rotation
4 Hip joint
5 Mechanical axis
6 Tibia
7 Measurement device
7.1, 7.2 Camera
7.3 Evaluation device
7.4 Control device (progress control)
8, 8', 9 Multi-point indicator
8A Clamping device
10 Cutting jig
10A Jig adapter
10B, 10C Electric motor
30 Spherical surface path
31 Center of the spheres
32 Measurement point
33 Local coordinate system
34 Global coordinate system
40 Measurement of point coordinates
41 Section text
43 Eliminate measurement-point-coordinate set
44 Expurgate measurement-point-coordinate set
45 Expurgated measurement-point-coordinate set
46 Carry out error-minimizing calculation with statistics
47 Check whether limiting value has been exceeded
48 Reject measurement-point-coordinate set with maximal improvement values
49 Store coordinates of the rotation center with statistics
50 Check the possibility of eliminating a maximal/minimal improvement value
51 Reject measurement-point-coordinate set
52 Statistical testing of stored coordinates
53 Display coordinates of the center of rotation
60 Sequence with respect to the femur
61 Tactile sampling in the knee
62 Tactile sampling of the epicondyles/Whiteside line, with error minimization
63 Calculation of a directional vector of locomotion
64 No precise result found
65 Precise result found
66 Identify position of hip-joint center
67 Start a necessary measurement
68 Carry out calculation for the center of rotation
69 Precise result found
70 No precise result found
71 Calculation of the alignment parameter of the intersection point
72 Repetition of the process if intersection point not aligned
73 Establish that cutting jig is aligned
74 Display of the femur
75 Display of the femur and the tibia
76 Quality management, control measurement, data collection for correction models etc.

What is claimed is:

1. A method of finding the position of a mechanical axis running in the longitudinal direction through a limb, the limb rotatably supported by a first end via a movable and inaccessible center of rotation for the mechanical determination of coordinates, comprising:

providing an optical coordinate-measurement device with at least one multi-point indicator to signal measurement-point coordinates in a rotational position of the limb;

rigidly attaching said multi point indicator near a second end of the limb;

detecting several measurement-point coordinates ($P_{11}$, $P_{21}$, $P_{31}$, $P_{n1}$) per rotational position of the limb;

recording said measurement-point coordinates;

selecting from measurement-point-coordinate sets ($P_{11}$–$P_{n1}$, $P_{12}$–$P_{n2}$, $P_{1m}$–$P_{nm}$) at least one group;

assigning said at least one group to a same site of the center of rotation; and calculating the position of the first end of the limb and a mechanical axis running through the first and second ends using the measurement-point-coordinate sets ($P_{11}$–$P_{n1}$, $P_{12}$–$P_{n2}$, $P_{1m}$–$P_{nm}$) assigned to said site of the center of rotation without piercing a skin of the limb above said second end.

2. The method according to claim 1, further comprising:

calculating several spherical surfaces that represent paths through which the second end of the limb moves from the at least one group of measurement point coordinate sets ($P_{11}$–$P_{n1}$, $P_{12}$–$P_{n2}$, $P_{1m}$–$P_{nm}$) assigned to said same site of the center of rotation; and calculating the coordinates of a point on which said spherical surfaces are centered to represent the center of rotation of the limb as a point on the mechanical axis, said calculation employing the equation position $P_{(n\ m)}$ relative to $P_{(n+i\ m)}$=position $P_{(n\ m+j)}$ relative to $P_{(n+im+j)}$.

3. The method of claim 1, wherein the selection of the at least one group of measurement-point-coordinate sets ($P_{11}$–$P_{n1}$, $P_{12}$–$P_{n2}$, $P_{1m}$–$P_{nm}$) from a number of sets that have been collected in a plurality of rotational positions of the limb is performed by proceeding through several steps of an iteration procedure, in each step of which one measurement-point-coordinate set is eliminated and an improvement thereby achieved is evaluated.

4. The method according to claim 3, wherein the evaluation is accomplished by means of an iterative calculation by a least-squares method.

5. The method of claim 1, further comprising:

calibrating the multi-point indicator before beginning the collection of the measurement-point coordinates;

comparing measurement-point coordinate relations resulting from said calibration with the relations of the recorded measurement-point coordinates for every rotational position of the limb; and deleting a measurement-point-coordinate set lying outside a predetermined tolerance limit.

6. The method of claim 1, further comprising specifying a second point required for the calculation of the mechanical axis, in terms of bony reference points by employing the optical coordinate measurement device with an additional indicator, said second point situated at the second end of the limb.

7. The method of claim 1, wherein the steps involved in the determination of the mechanical axis are carried out with computer assistance, such that the instructions regarding the actions needed to put the limb in particular rotational positions and information about the intermediate results of the relevant steps are displayed in a menu-guided environment.

8. The method of claim 1, further comprising aligning a cutting jig with respect to the mechanical axis that has been identified for the mechanical processing of the second end of the limb.

9. The method according to claim 8, wherein the identified mechanical axis is indicated by an adapter or multi-point indicator that is fixedly attached to the limb, and the cutting jig is aligned with respect to said adapter or multi-point indicator with by a calibrated jig adapter.

10. The method of claim 9, further comprising carrying out a translational adjustment of the cutting jig with respect to the adapter by tactile sampling of the cutting jig with an accessory indicator employing the coordinate-measurement device.

11. An arrangement for finding the position of a mechanical axis of a limb that is rotatably supported by its first end via a movable center of rotation comprising:

a camera arrangement with at least two cameras spaced apart from one another by a fixed distance for the spatially determined reception of transmitter signals at least two multi-point indicators, each of which comprises a measurement-point field with several measurement points, to detect several measurement-point coordinates ($P_{11}$–$P_{n-1}$), such that a first multi-point indicator is constructed as a movable feeler for the tactile sampling of bony reference points in order to measure their coordinates, and an evaluation unit for evaluating the measurement-point coordinate sets provided by the multi-point indicator and detected by the camera arrangement, in order to identify the mechanical axis of the limb extending through the first end of the limb without piercing a skin on the limb above a second end of the limb, and such that a second multi-point indicator is rigidly attached in the vicinity of said second end of the limb, in such a way that it provides measurement-point-coordinate sets for several rotational positions of the limb, all of which lie on spherical surfaces positioned around the associated site of the center of the rotation, and a process control means to control sequential recording and storage of the measurement-point-coordinate sets obtained in the individual rotational positions of the limb, and subsequent processing thereof, according to a prespecified processing thereof, according to a prespecified processing sequence, and wherein the evaluation device comprises means for performing an iteration procedure, to specify a site of the center of rotation, for calculating the position of a mechanical axis on the basis of the site of the center of rotation, and for calculating a second point at the second end of the limb, specified on the basis of bony reference points on the limb.

12. The arrangement according to claim 11, further comprising an adjustable clamping device to serve as an adapter for fixating the second multi-point indicator near the second end of the limb.

13. The arrangement according to claim 11, further comprising a calibrated jig adapter that, can be connected both to the clamping device and to a cutting jig for the mechanical processing of the second end of the limb, said connection being in such a way that these elements cannot be rotated but are capable of translational displacement, so that the cutting jig can be aligned with the mechanical axis by way of the jig adapter and can be displaced along the alignment axis.

14. The arrangement according to claim 13, wherein the first multi-point indicator, which is designed as a tactile sampler, also serves as an indicator for detecting the current position of the cutting jig.

15. The arrangement according to claim 11, further comprising display and input means associated with the process control means and the evaluation unit, in order to implement at least one of an optical and acoustical menu guidance for the determination of the center of rotation and the mechanical axis.

16. The arrangement according to claim 15, wherein the menu guidance also comprises display and input means for positioning of the cutting jig.

17. The arrangement according to claim 11, wherein at least the second multipoint indicator comprises a plurality of IR light-emitting diodes as active transmitters of measurement-point coordinates, which are disposed in an indicator base constructed in tripod form.

18. The arrangement according to claim 13, further comprising display and input means associated with the process control means and the evaluation unit in order to implement at least on of an optical and acoustical menu guidance for the determination of the center of rotation and the mechanical axis and electric motors connected to the jig adapter for the translational displacement of the cutting jig with respect to the mechanical axis, and wherein the motors are driven in particular by control signals input in the context of the menu guidance.

19. The method of claim 5, wherein comparing the measurement-point-coordinate relations resulting from the calibration with the relations of the recorded measurement-point coordinates comprises a plausibility consideration.

20. The arrangement of claim 11, wherein the means for performing an iteration procedure employs an error-minimization calculation according to a least-squares method.

* * * * *

UNITED STATES PATENT AND TRADEMARK OFFICE
CERTIFICATE OF CORRECTION

PATENT NO.        : 6,928,742 B2
APPLICATION NO. : 10/363488
DATED             : August 16, 2005
INVENTOR(S)       : Holger Broers et al.

It is certified that error appears in the above-identified patent and that said Letters Patent is hereby corrected as shown below:

In column 5 at line 40 (Approx.), Delete "Susequently" and insert -- Subsequently, --, therefor.

In column 13 at line 40 (Approx.), In Claim 3, after "from a" insert -- total --.

In column 13 at line 60, In Claim 6, delete "axis," and insert -- axis --, therefor.

In column 14 at line 12 (Approx.), In Claim 9, after "with" delete "by".

In column 14 at line 61, In Claim 13, delete "that," and insert -- that --, therefor.

In column 16 at line 2, In Claim 18, after "least" delete "on" and insert -- one --, therefor.

In column 16 at line 7-8 (Approx.), In Claim 18, after "driven" delete "in particular".

Signed and Sealed this

Seventh Day of August, 2007

JON W. DUDAS
*Director of the United States Patent and Trademark Office*